US 11,346,753 B2
United States Patent
Turgul et al.

(10) Patent No.: US 11,346,753 B2
(45) Date of Patent: May 31, 2022

(54) IMPACTOR FOR AEROSOL COMPONENT COLLECTION

(71) Applicant: University of Northumbria at Newcastle, Newcastle upon Tyne (GB)

(72) Inventors: Volkan Turgul, London (GB); Sterghios Moschos, Newcastle upon Tyne (GB); Izzet Kale, London (GB)

(73) Assignee: University of Northumbria at Newcastle, Tyne And Wear (GB)

( * ) Notice: Subject to any disclaimer, the term of this patent is extended or adjusted under 35 U.S.C. 154(b) by 264 days.

(21) Appl. No.: 16/645,893

(22) PCT Filed: Sep. 12, 2018

(86) PCT No.: PCT/GB2018/052588
§ 371 (c)(1),
(2) Date: Mar. 10, 2020

(87) PCT Pub. No.: WO2019/053423
PCT Pub. Date: Mar. 21, 2019

(65) Prior Publication Data
US 2020/0278275 A1    Sep. 3, 2020

(30) Foreign Application Priority Data

Sep. 12, 2017 (GB) .................................... 1714669

(51) Int. Cl.
*G01N 1/22* (2006.01)
*G01N 33/497* (2006.01)
(52) U.S. Cl.
CPC ......... *G01N 1/2208* (2013.01); *G01N 33/497* (2013.01)
(58) Field of Classification Search
CPC ......... G01N 2001/2223; G01N 1/2208; G01N 1/2205; G01N 1/2273; G01N 2001/2288;
(Continued)

(56) References Cited

U.S. PATENT DOCUMENTS 2,894,877 A * 7/1959 Sinden .................. C12M 27/10
435/309.1
3,966,439 A * 6/1976 Vennos ................ G01N 1/2205
73/863.22
(Continued)

FOREIGN PATENT DOCUMENTS

CN    202420926 U  *  9/2012
CN    214702896 U  *  11/2021
(Continued)

OTHER PUBLICATIONS

Combined Search and Examination Report for United Kingdom Application No. GB 1714669.7 dated Feb. 27, 2018.
(Continued)

*Primary Examiner* — David A. Rogers
(74) *Attorney, Agent, or Firm* — Wolf, Greenfield & Sacks, P.C.

(57) ABSTRACT

There is provided a kit of parts for assembly into an impactor (100) for aerosol component collection, such as for exhaled breath. The kit of parts is configured such that an impactor component (128) is receivable into the assembly such that, when a sealing component (136) is in a sample collection configuration and an aerosol sample is being received at an aerosol inlet (110) of a housing of the kit, in use, an aerosol flow path (124) of the aerosol sample is directed onto an impaction surface (130) of the impactor component (128) to promote aerosol deposition thereon. The kit of parts is further configured such that the sealing component (136) is changeable in the assembly into a sample containment configuration before removal of the impactor component (128) from the assembly, so as to retain any aerosol components deposited on the impaction surface (130).

19 Claims, 6 Drawing Sheets

(58) Field of Classification Search
CPC ... G01N 2001/2285; G01N 2015/0288; G01N 2001/4088; G01N 2015/0038; B01L 3/5023
See application file for complete search history.

(56) References Cited

U.S. PATENT DOCUMENTS

| | | | | |
|---|---|---|---|---|
| 3,983,743 | A * | 10/1976 | Olin | G01N 1/2247 73/28.06 |
| 4,133,202 | A * | 1/1979 | Marple | G01N 15/0255 73/28.04 |
| 4,155,247 | A * | 5/1979 | Kaczmarek | G01N 1/2202 73/863.23 |
| 4,249,655 | A * | 2/1981 | Patureau | B01D 50/002 209/237 |
| 4,255,172 | A * | 3/1981 | Smith | B01D 45/08 55/319 |
| 4,277,259 | A * | 7/1981 | Rounbehler | G01N 1/2273 220/379 |
| 4,321,822 | A | 3/1982 | Marple et al. | |
| 4,350,037 | A * | 9/1982 | Higham | G01N 1/2273 422/88 |
| 4,640,140 | A * | 2/1987 | Burghoffer | G01N 15/0255 73/863.22 |
| 4,675,034 | A * | 6/1987 | Lynch | G01N 1/2205 55/504 |
| 4,796,475 | A * | 1/1989 | Marple | G01N 1/2205 422/70 |
| 4,827,779 | A | 5/1989 | Marple et al. | |
| 4,941,899 | A * | 7/1990 | Liu | G01N 1/2211 55/337 |
| 4,961,916 | A * | 10/1990 | Lesage | B01D 53/30 422/109 |
| 5,092,218 | A * | 3/1992 | Fine | G01N 1/02 436/156 |
| 5,898,114 | A * | 4/1999 | Basch | G01N 1/2205 73/863.23 |
| 5,977,547 | A * | 11/1999 | Phillips | G01T 7/04 250/393 |
| 6,023,981 | A * | 2/2000 | Phillips | G01N 1/2205 73/863.23 |
| 6,101,886 | A * | 8/2000 | Brenizer | B01D 45/08 55/308 |
| 6,267,016 | B1 * | 7/2001 | Call | G01N 1/2273 73/863.22 |
| 6,272,937 | B1 * | 8/2001 | Mengel | G01N 1/2273 422/64 |
| 6,463,814 | B1 * | 10/2002 | Letarte | G01N 1/2208 73/863.22 |
| 6,468,330 | B1 * | 10/2002 | Irving | B01D 17/00 95/219 |
| 6,472,203 | B1 * | 10/2002 | Gallup | C12M 23/10 435/305.4 |
| 6,520,034 | B1 * | 2/2003 | Masquelier | G01N 1/2273 209/17 |
| 6,532,835 | B1 * | 3/2003 | Saaski | G01N 1/2273 73/863.21 |
| 6,607,700 | B1 * | 8/2003 | Apte | G01N 33/004 422/91 |
| 6,692,553 | B2 * | 2/2004 | Jordan, Sr. | B01D 45/10 55/435 |
| 6,729,196 | B2 * | 5/2004 | Moler | B01D 21/2455 73/863.22 |
| 7,062,982 | B2 * | 6/2006 | Coyle | B01D 50/004 73/863.23 |
| 7,243,560 | B2 * | 7/2007 | Coyle | G01N 1/2208 73/28.02 |
| 7,334,453 | B2 * | 2/2008 | Trakumas | G01N 1/2208 73/28.01 |
| 7,458,284 | B2 * | 12/2008 | Shih | G01N 1/2208 73/863.21 |
| 7,597,015 | B2 * | 10/2009 | Harley | G01N 1/2208 73/28.05 |
| 7,785,408 | B2 * | 8/2010 | Jordan, Sr. | B01D 45/10 96/413 |
| 7,998,731 | B2 * | 8/2011 | Daitch | G01N 1/2273 435/309.1 |
| 8,082,808 | B2 * | 12/2011 | Freeman | G01N 1/2273 73/863.21 |
| 8,104,362 | B2 * | 1/2012 | McFarland | B01D 46/06 73/863.21 |
| 8,425,642 | B2 * | 4/2013 | Worker | B04C 5/28 55/345 |
| 8,578,796 | B2 * | 11/2013 | Cho | G01N 1/24 73/863.11 |
| 8,584,536 | B2 * | 11/2013 | Page | B01D 46/0067 73/863.24 |
| 8,671,738 | B2 * | 3/2014 | Witham | B01D 46/10 73/28.05 |
| 8,689,648 | B1 * | 4/2014 | Heff | G01N 1/2273 73/863.22 |
| 8,991,271 | B2 * | 3/2015 | Uang | G01N 15/0606 73/863.22 |
| 9,086,341 | B2 * | 7/2015 | Tsai | G01N 1/2208 |
| 9,121,845 | B2 * | 9/2015 | Vellutato, Jr. | G01N 33/497 |
| 9,182,320 | B2 * | 11/2015 | Ewing | G01N 1/2205 |
| 9,457,348 | B2 * | 10/2016 | Clavaguera | G01N 1/2205 |
| 9,506,843 | B2 * | 11/2016 | Peters | G01N 1/2208 |
| 9,513,278 | B2 * | 12/2016 | Vellutato, Jr. | G01N 33/497 |
| 10,345,200 | B2 * | 7/2019 | Scialo | G01N 1/2273 |
| 10,401,263 | B2 * | 9/2019 | Clavaguera | G01N 1/2208 |
| 10,488,305 | B2 * | 11/2019 | Miller-Lionberg | G01N 1/2273 |
| 10,571,369 | B2 * | 2/2020 | Vellutato, Jr. | G01N 1/22 |
| 10,753,829 | B2 * | 8/2020 | Novosselov | G01N 1/02 |
| 2001/0013244 | A1 | 8/2001 | Marple et al. | |
| 2002/0066321 | A1 * | 6/2002 | Lagraff | G01N 15/00 73/863.22 |
| 2005/0279181 | A1 * | 12/2005 | Trakumas | G01N 1/2208 73/863.22 |
| 2005/0279182 | A1 * | 12/2005 | Cole | G01N 1/2273 73/864.71 |
| 2008/0233636 | A1 * | 9/2008 | Ryan | G01N 1/2273 435/287.9 |
| 2009/0056417 | A1 | 3/2009 | Kilps et al. | |
| 2009/0272202 | A1 * | 11/2009 | Uang | G01N 1/2205 73/863.23 |
| 2010/0212436 | A1 | 8/2010 | Swenson et al. | |
| 2012/0247233 | A1 | 10/2012 | Maheshwari | |
| 2015/0212081 | A1 * | 7/2015 | Catteruccia | B01L 3/5029 435/5 |

FOREIGN PATENT DOCUMENTS

| | | | | |
|---|---|---|---|---|
| EP | 2758763 B1 * | 4/2018 | | G01N 1/2208 |
| FR | 2588662 A1 * | 4/1987 | | G01N 1/2205 |
| WO | WO 2001/84108 A2 | 11/2001 | | |

OTHER PUBLICATIONS

International Preliminary Report on Patentability for International Application No. PCT/GB2018/052588 dated Mar. 26, 2020.
International Search Report and Written Opinion for International Application No. PCT/GB2018/052588 dated Jan. 3, 2019.

* cited by examiner

IMPACTOR FOR AEROSOL COMPONENT COLLECTION

CROSS-REFERENCE TO RELATED APPLICATIONS

This application is a national stage filing under 35 U.S.C. § 371 of international application number PCT/GB2018/052588, filed Sep. 12, 2018, which claims the benefit of British application number 1714669.7, filed Sep. 12, 2017, each of which is herein incorporated by reference in its entirety.

This application is concerned with breath collection and analysis. In particular, this application discloses an impactor apparatus for aerosol component collection, such as for exhaled breath component collection, a kit of parts for the impactor apparatus and a method of extracting aerosol components from a carrier gas.

BACKGROUND

Exhaled breath can be collected for analysis, for example for use in monitoring a physiology of a subject, particularly the breathing system thereof, or in indicating an airway disease.

It is known to collect breath by passing exhaled breath directly through a cooled collection vessel in order to encourage condensation and collection of exhaled breath vapour. The condensed exhaled breath is deposited in the collection vessel, whilst non-condensed breath components continue out of the collection vessel.

It is in this context that the present invention has been devised.

BRIEF SUMMARY OF THE DISCLOSURE

The known exhaled breath condensate collection devices collect breath by condensation of all breath components together.

Exhaled breath typically contains a mixture of different components in gas phase (such as vapour) acting as a carrier for liquid phase components (which may condense from the carrier gas) and as solid phase components, such as liquid and solid particulates, and as such is an aerosol.

The inventors have realised that it would be beneficial if breath could be collected so as to enable differentiation and separation of constituent components of breath on collection. Collection of these components, for example by isolating aerosol components having particular characteristics, such as size, or separately collecting breath solid or liquid aerosol components of different sizes, would enable a more detailed analysis of breath and the condition of a patient's breathing system and physiology.

Thus, in accordance with the present disclosure there is provided a kit of parts for assembly into an impactor for aerosol component collection, such as for exhaled breath. The kit comprises a housing configured to define an aerosol inlet for receiving an aerosol sample in use and, when the kit of parts is assembled into the impactor, to define at least in part an aerosol flow path from the aerosol inlet through the impactor apparatus. The kit further comprises an impactor component receivable into an assembly providing the impactor apparatus. The assembly comprises at least the housing. The impactor component has an impaction surface onto which one or more aerosol components from the aerosol sample are to be deposited in use. The kit further comprises a sealing component for sealing around the impaction surface of the impactor component. The sealing component is changeable from a sample collection configuration in which the impaction surface is exposed for aerosol component collection to a sample containment configuration in which the impaction surface is isolated from the external environment. The kit of parts is configured such that the impactor component is receivable into the assembly such that, when the sealing mechanism is in the sample collection configuration and an aerosol sample is being received at the aerosol inlet in use, the aerosol flow path of the aerosol sample is directed onto the impaction surface to promote aerosol deposition thereon. The kit of parts is further configured such that the sealing component is changeable in the assembly into the sample containment configuration before removal of the impactor component from the assembly, so as to retain any aerosol components deposited on the impaction surface.

Cascade impactors, for example Andersen cascade impactors, are known for use in analysing the distribution of sizes of solid particulates produced from an aerosolised dry powder drugs product administered through inhalers. The aerosolised dry powder inhaler particles are passed through the impactor where components of different sizes are collected by impaction against successive impactor plates.

The impactor apparatus assembled from the kit of parts in accordance with the above aspect of the invention is usable to collect and retain for analysis components of exhaled breath through aerosol deposition thereof resulting from impaction of the breath on the impaction surface in use. The impactor is provided with a sealing mechanism enabling a sealing component to be moveable into the sample containment configuration before removal of the impactor component from the assembly, so as to retain any aerosol components deposited on the impaction surface. This avoids loss of the impacted exhaled breath sample due to evaporation of liquid components from the impaction surface following collection. Sealing the impaction component before removal from the assembly ensures that the impacted breath sample is retained for analysis, whereas its liquid components could otherwise evaporate back into the gas phase of the surrounding air. Sealing of the impaction component before removal of the sample also ensures that the sample deposited thereon is not contaminated following collection.

The inventors have realised that impactors of the prior art cannot be used to effectively collect components of breath for analysis as the collected breath samples can evaporate and become contaminated after collection.

The impactor apparatus assembled from the kit of parts in accordance with the above aspect of the invention provides a mechanism for retaining the impacted breath components in a sealed environment following collection, preventing sample loss and contamination.

Thus, sample contamination and/or sample loss for the collected aerosol components of an aerosol sample can be substantially prevented using a sealing component to seal around the impaction surface of the impactor component before the impactor component is removed from the assembly.

One or more parts of the kit of parts separately or together may provide a sealing mechanism which is configured and/or operable such that the sealing component is moved or caused to be moved into the sample containment configuration after sample collection before the impactor component is fully removed from the assembly.

Thus, when the impactor component is fully removed from the assembly, the sealing component is already in the sample containment configuration and substantially all aerosol components deposited on the impaction surface are retained.

The housing may comprise an inlet housing portion, defining the aerosol inlet therein. The housing may comprise an outlet housing portion, defining an aerosol outlet therein. The aerosol outlet may be in fluid communication with the aerosol inlet through the impactor apparatus when the kit of parts is assembled.

The aerosol inlet may be provided with an inlet pressure valve to substantially prevent airflow in reverse through the impactor apparatus from the aerosol outlet towards the aerosol inlet. The inlet pressure valve may further be configured to prevent ingress of gas into the impactor apparatus through the aerosol inlet unless the gas is above a predetermined inlet pressure threshold. In embodiments, the predetermined inlet pressure threshold may be changed based on an external environment of the impactor apparatus. In other embodiments, the predetermined inlet pressure threshold may be a fixed pressure threshold which does not vary with an external environment of the impactor apparatus.

The aerosol outlet may be provided with an outlet pressure valve to substantially prevent airflow in reverse through the impactor apparatus from the aerosol outlet towards the aerosol inlet. The inlet pressure valve may further be configured to prevent transfer of gas out from the impactor apparatus through the aerosol outlet unless there exists a pressure differential across the outlet pressure valve above a predetermined outlet pressure threshold. In embodiments, the predetermined outlet pressure threshold may be changed based on an external environment of the impactor apparatus. In other embodiments, the predetermined outlet pressure threshold may be a fixed pressure threshold which does not vary with an external environment of the impactor apparatus.

Thus, contamination of an internal space of the impactor apparatus may be substantially prevented through use of one or more pressure valves.

It will be understood that the predetermined inlet pressure threshold based on the external environment of the impactor apparatus may be determined electronically or independently. It will similarly be understood that the predetermined outlet pressure threshold based on the external environment of the impactor apparatus may be determined electronically or independently.

The housing may comprise at least one impactor housing portion to receive the impactor component therein during assembly of the kit of parts.

The impactor component may be a receptacle or container, such as a shallow dish. In alternative examples, the impactor component may be provided by a large volume container to allow for the collection of a large volume of aerosol components. Thus, the impactor component may be suitable for protracted use. The large volume of aerosol components may be at least 50 millilitres of aerosol components. In some embodiments, the large volume of components may be at least 1 litre of aerosol components. The impaction surface may be provided by a base surface of the receptacle, such as a base surface of the dish.

The assembly providing the impactor apparatus may be configured, when assembled, to control a temperature of the impactor component to be at a predetermined temperature. The predetermined temperature may be between minus 80 degrees Celsius to 40 degrees Celsius. In embodiments, the impactor apparatus may be configured, when assembled to control a temperature of the impactor apparatus to be at the predetermined temperature. Thus, the temperature of the impactor apparatus can be maintained at a temperature to substantially prevent any sample loss or contamination through evaporation after and during sample collection. In embodiments, the predetermined temperature may be lower than a temperature of the aerosol sample on entry to the impactor apparatus. In embodiments, the predetermined temperature may be lower than an ambient environmental temperature. It will be understood that the temperature control of the impactor component may be achieved using a Peltier cooler, or other heat exchange component. In some embodiments, the heat exchange component is arranged to directly contact the impactor component whereby to facilitate direct heat transfer to or away from the impactor component. Reducing a temperature of the impactor component has been seen to improve a collection efficiency of the impactor apparatus.

The assembly providing the impactor apparatus may have defined therein a plurality of flow constrictions upstream of the impactor component in the aerosol flow path and configured to generate a high-velocity aerosol flow onto the impaction surface in the aerosol flow path. Thus, a plurality of high-velocity jets of aerosol may flow onto the impaction surface and cause deposition thereon of aerosol components at multiple locations across the impaction surface.

The plurality of flow constrictions may be at least ten flow constrictions. The flow constrictions may have a length in a flow-wise direction at least as long as an extent of the flow constriction in a cross-flow direction. In some examples, a length of the flow constrictions may be at least 3 millimetres.

The plurality of flow constrictions may be defined in the housing. In embodiments, the plurality of flow constrictions may be defined in the impactor housing portion of the housing.

The kit of parts may comprise a plurality of the impactor components, each receivable into the assembly to be arranged in the assembly together successively in the aerosol flow path.

The impactor apparatus may be for collecting aerosol components having different characteristics in each of the plurality of impactor components. In embodiments, the impactor apparatus may be for collecting aerosol components of different size and/or mass in each of the plurality of impactor components.

The assembly may be configured such that, in the sample collection configuration, the aerosol flow path directed onto the impaction surface of the impactor component is directed, downstream, around an outer edge of the impactor component through the impactor apparatus. Thus, the aerosol flow path goes from the aerosol inlet, optionally through the one or more flow constrictions, onto the impaction surface, around the outer edge of the impactor component, and out of the apparatus via the aerosol outlet.

The sealing component may be a cover member to cover the impaction surface when the sealing component is in the sample containment configuration. The sealing component may be movable from the sample collection configuration to the sample containment configuration. Thus, a simple mechanical movement may be used to operate the sealing component.

The cover member may be a film seal movable to cover the impaction surface when the sealing component is in the sample containment configuration.

The cover member may be a rotary seal. The cover member may be a thermal seal. The cover member may be a pneumatic seal. The cover member may be a mechanical seal. The cover member may be an electromechanical seal. The cover member may be a chemical seal. The cover member may be a linear seal. The cover member may be a circular seal. The cover member may be a constricting seal. The cover member may be a spigot seal. The cover member may be a valve seal. The cover member may be a vacuum based seal.

The rotary seal may be an iris mechanism. The thermal seal may be a thermal sealing of plastics. The chemical seal may be a chemical glue seal. It will be appreciated that other sealing methods and mechanisms will be apparent to the person skilled in the art.

Additional sealing or resealing mechanisms may involve thermally activated seals, photochemically activated seals such as UV crosslinking or other compositive wavelength-reactive materials.

The operation of the sealing component may be manual. The operation of the sealing component may be controlled electronically.

The cover member may be slidable to move from an uncovered position allowing the aerosol flow path to be directed onto the impaction surface in the sample collection configuration to a covered position in which the cover member covers the impaction surface in the sample containment configuration to retain any aerosol components deposited on the impaction surface. In examples, it will be understood that the cover member, when covering the impaction surface, substantially prevents contamination of the impaction surface from an external environment of the impactor component.

The housing may have defined therein an opening for passage therethrough of the cover member onto the impactor component during movement from the sample collection configuration to the sample containment configuration.

The or a further sealing component of the kit of parts may be for sealing around the impaction surface of the impactor component. The kit of parts may be configured such that the or the further sealing component is changeable from a sealed configuration in which the impaction surface is isolated from the external environment to the sample collection configuration in which the impaction surface is exposed for aerosol collection.

The or the further sealing component may be a cover member to cover the impaction surface when the sealing component is in the sealed configuration. The sealing component may be movable from the sealed configuration to the sample collection configuration.

The housing may have defined therein an opening for passage therethrough of the cover member moving off the impactor component during movement from the sealed configuration to the sample collection configuration.

The housing may comprise an opening cover to selectively close the opening in the housing.

The kit of parts may further comprise a lid extraction component to cover the opening and for receipt of the cover member therein when the sealing component is in the sample collection configuration.

The kit of parts may further comprise a cover removal tool for insertion into the housing through the lid extraction component and to engage with the cover member for at least one of: movement of the cover member from the sealed configuration to the sample collection configuration; and movement of the cover member from the sample collection configuration to the sample containment configuration.

The sealing component may be lockable in the sample containment configuration.

The sealing component may be lockable by rotation of the sealing component relative to the impactor component.

The housing may be formed from a plurality of housing portions which, when the kit of parts is assembled into the impactor, receive the impactor component therein to substantially enclose the impactor component within the housing.

Viewed from another aspect, the present disclosure provides an impactor apparatus for aerosol component collection and formed from the kit of parts described hereinbefore.

Viewed from a further aspect, the present disclosure provides a method of collecting aerosol components from an aerosol sample in an impactor apparatus. The method comprises: assembling the impactor apparatus from at least a housing to receive an impactor component within the impactor apparatus. The housing defines, at least in part, an aerosol flow path from the aerosol inlet through the impactor apparatus. The impactor component has an impaction surface onto which one or more aerosol components from the aerosol sample are to be deposited in use. The impactor component is provided with a sealing component for sealing around the impaction surface of the impactor component. The sealing component is in a sample collection configuration in which the impaction surface is exposed for aerosol component collection. The aerosol flow path of the aerosol sample is directed onto the impaction surface to promote aerosol deposition thereon. The method further comprises supplying an aerosol sample to an aerosol inlet of a housing of the impactor apparatus to deposit one or more aerosol components of the aerosol sample onto the impaction surface. The method further comprises changing the sealing component from the sample collection configuration to a sample containment configuration in which the impaction surface is isolated from the external environment. The sealing component is changed from the sample collection configuration into the sample containment configuration before removal of the impactor component from the assembly, so as to retain any aerosol components deposited on the impaction surface.

Although the discussion above has focused in parts on analysis of exhaled breath, it will be understood that the disclosure above can equally be applied to any aerosol sample for collection of aerosol components. For example, the aerosol may be a pharmaceutical aerosol, such as an aerosol expelled from a nebuliser. In other examples, the aerosol may be an environmentally generated aerosol, and animal generated aerosol, or an instrument generated aerosol.

BRIEF DESCRIPTION OF THE DRAWINGS

Embodiments of the invention are further described hereinafter with reference to the accompanying drawings, in which.

DETAILED DESCRIPTION

Figure 1:
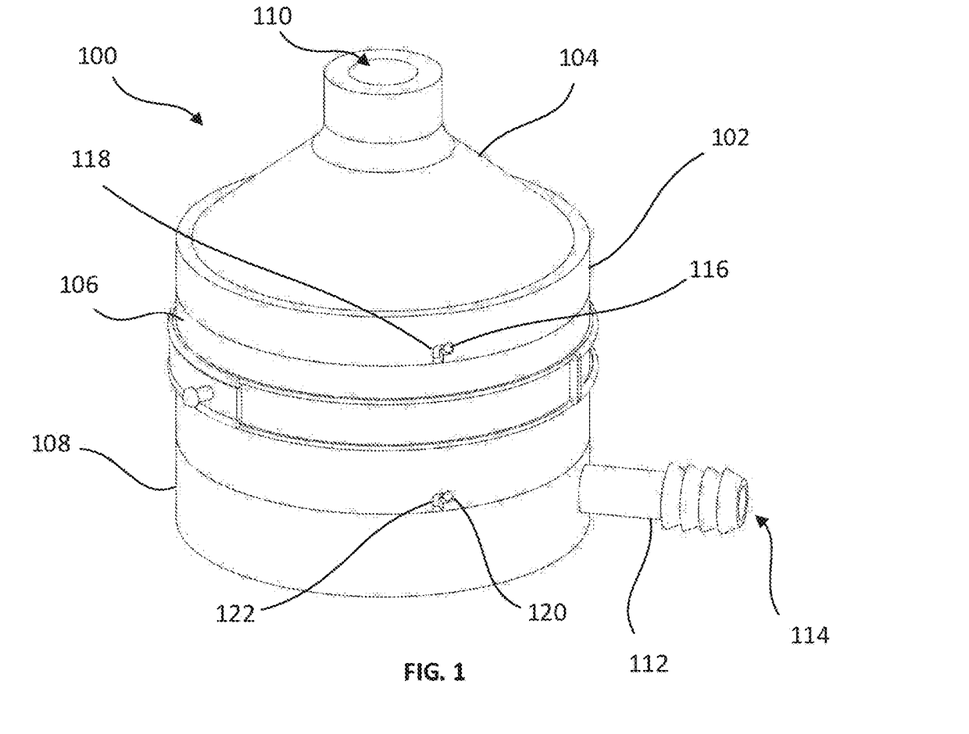
FIG. 1 is a diagram showing an impactor apparatus for aerosol component collection.

FIG. 1 is a diagram showing an impactor apparatus for aerosol component collection. The impactor apparatus 100 comprises a housing assembly 102 which defines an aerosol flow path (not shown in FIG. 1) through the impactor apparatus 100. The housing assembly 102 comprises an inlet housing portion 104 and an impactor housing portion 106. In this example, the housing assembly 102 further comprises an outlet housing portion 108. The inlet housing portion 104 defines an aerosol inlet 110 at an end thereof. The aerosol inlet 110 is for receiving an aerosol sample. In examples, the aerosol inlet 110 may be connected to further components. For example, where the impactor apparatus 100 is for use with exhaled breath, the aerosol inlet 110 may be connected to a mouthpiece module for receiving exhaled breath from a user. Alternatively, where the impactor apparatus 100 is for use with inhaled drug analysis, the aerosol inlet 110 may be connected directly or indirectly to a receptacle for storing the inhaled drug, for example an inhaler. The aerosol flow path is defined from the aerosol inlet 110 through the impactor apparatus 100. The impactor housing portion 106 is provided between the inlet housing portion 104 and the outlet housing portion 108. In this example, the outlet housing portion 108 comprises an outlet pipe 112 for connection to a further component and defining an aerosol outlet 114. The aerosol outlet 114 is in fluid communication with the aerosol inlet 110 via the aerosol flow path through the impactor apparatus 100 and in particular through the impactor housing portion 108. In this example, the outlet pipe 112 is for resilient insertion to a connecting tube. In some examples, the outlet pipe 112 may be connected to a suction pump (not shown).

As will be described in further detail below, in examples, the housing assembly 102 can be assembled from the inlet housing portion 104, one or more impactor housing portions 106 and the outlet housing portion 108. The housing assembly 102 can also be disassembled into separate parts. For assembly, the inlet housing portion 104 can be secured to the impactor housing portion 106 by securing means. In this example, the securing means is in the form of an impactor housing protrusion 116 protruding radially outward from a side wall of the impactor housing portion 106 and a dog-leg cut out 118 defined in a side wall of the inlet housing portion 104. The impactor housing protrusion 116 and the dog-leg cut out 118 are configured such that when the impactor housing protrusion 116 is engaged in the dog-leg cut out 118, the inlet housing portion 104 is secured to the impactor housing portion 106. In this example, the impactor housing portion 106 comprises three impactor housing protrusions 116 circumferentially spaced around the side wall of the impactor housing portion 106 and the side wall of the inlet housing portion 104 has defined therein three corresponding dog-leg cut outs 118 circumferentially spaced around the side wall of the inlet housing portion 104. Thus, the inlet housing portion 104 can be easily and releasably secured to the impactor housing portion 106. It will be understood that alternative securing means would be apparent to the skilled person, such as a screw connection, one or more clamps, bootstraps, or other fasteners.

In a similar way, the impactor housing portion 106 can be secured to the outlet housing portion 108 by securing means. In this example, the securing means is substantially the same as the securing means used to secure the inlet housing portion 104 to the impactor housing portion 106. In this example, the securing means is in the form of an outlet housing protrusion 120 protruding radially outward from a side wall of the outlet housing portion 108 and a dog-leg cut out 122 defined in a side wall of the impactor housing portion 106. The outlet housing protrusion 120 and the dog-leg cut out 122 are configured such that when the outlet housing protrusion 120 is engaged in the dog-leg cut out 122, the impactor housing portion 106 is secured to the outlet housing portion 108. In this example, the outlet housing portion 108 comprises three outlet housing protrusions 120 circumferentially spaced around the side wall of the outlet housing portion 108 and the side wall of the impactor housing portion 106 has defined therein three corresponding dog-leg cut outs 122 circumferentially spaced around the side wall of the impactor housing portion 106. Thus, the impactor housing portion 106 can be easily and releasably secured to the outlet housing portion 108.

Figure 2:
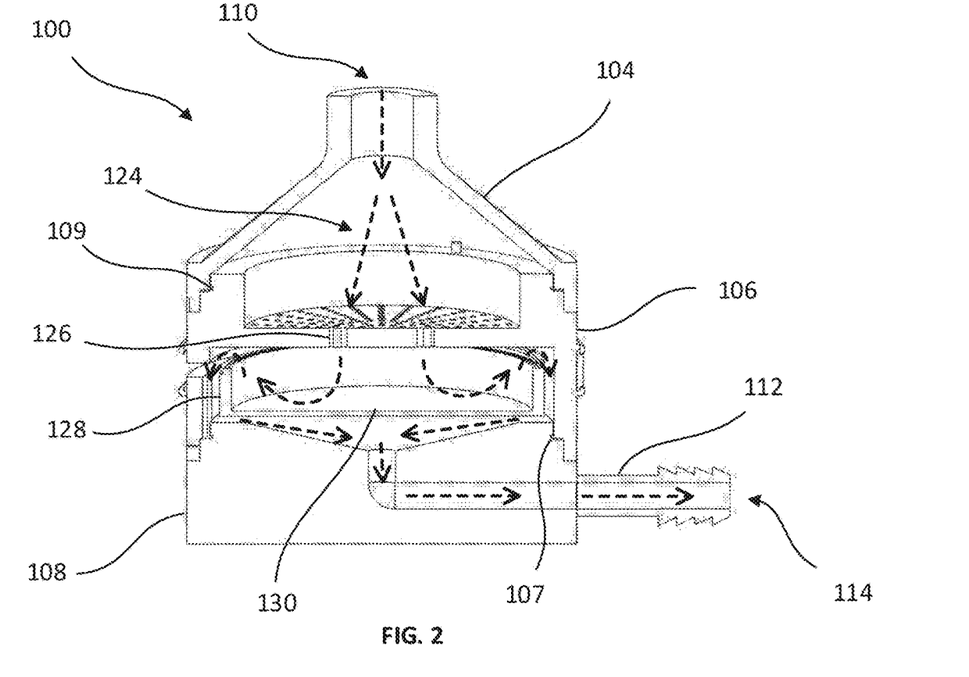
FIG. 2 is a cross-section through the impactor apparatus shown in FIG. 1.

FIG. 2 shows a cross-section through the impactor apparatus 100 shown in FIG. 1. An aerosol flow path 124 is shown schematically in FIG. 2 by a series of dotted arrows. The aerosol flow path 124 shows an aerosol sample enters the impactor apparatus 100 through the aerosol inlet 110. The aerosol sample then passes to the impactor housing portion 106 and on to the outlet housing portion 108 and out of the impactor apparatus 100 through the aerosol outlet 114.

As can be seen in FIG. 2, the impactor housing portion 106 has defined therein a plurality of flow constrictions 126 to generate a high-velocity aerosol flow in the form of jets. In the configuration of the impactor apparatus 100 shown in FIG. 2, which is a sample collection configuration, the impactor housing portion 106 also includes an impactor component 128 in the form of a receptacle which defines an impaction surface 130. The impactor component 128 is receivable into the rest of the impactor apparatus 100 in use and is spaced from an internal wall of the impactor housing portion 106 such that the aerosol flow path 124 continues from the flow constrictions 126, turning to flow along the impaction surface 130 and around an outer edge of the impactor component 128. The impactor component 128 is spaced from an upper surface of the outlet housing portion 108 whereby to allow the aerosol flow path 124 to continue under the impactor component 128, into the outlet housing portion 108 and out of the impactor apparatus 100 through the aerosol outlet 114. In this example, the impactor component 128 is a dish, such as a shallow dish, having the impaction surface as a base internal surface thereof. A height of a side wall of the impactor component 128 in this example is approximately 8 millimetres. In other examples, the height of the side wall of an impactor component may be as low as 3 millimetres. In further examples, the height of the side wall of an impactor component may be up to 2 centimetres, or more. It will be understood that at least the impactor housing portion 106 may be shaped to surround an impactor component 128 having a predetermined size.

In this example, the inlet housing portion 104, the impactor housing portion 106 and the outlet housing portion 108 are provided with respective sealing members 107, 109 therebetween such that, when the inlet housing portion 104 is secured to the impactor housing portion 106 and when the impactor housing portion 106 is secured to the outlet housing portion 108, as shown in FIG. 2, the egress or ingress of gasses or other contaminants or aerosol components between a side wall of the inlet housing portion 104 and a side wall of the impactor housing portion 106 or between a side wall of the impactor housing portion 106 and a side wall of the outlet housing portion 108 is substantially prevented. Thus, an internal space of the housing assembly 102 defined by the inlet housing portion 104, the impactor housing portion 106 and the outlet housing portion 108 is substantially isolated from an external environment of the impactor apparatus 100. In this example, the sealing members 107, 109 between the housing portions are each ring seals. The ring seal in this example is an O-ring formed from a resilient material, such as neoprene. It will be understood that alternative sealing members between the housing portions 104, 106, 108 of the housing assembly 102 may be suitable and apparent to the skilled person.

As will be appreciated, the aerosol sample, such as exhaled breath, to be introduced into the aerosol inlet 110 of the impactor apparatus 100 in use, may contain one or more aerosol components, such as droplets of liquid or particulates. The aerosol components will be entrained in the aerosol sample following the aerosol flow path 124. The aerosol sample flows through the flow constrictions 126 and is directed onto the impaction surface 130, but must turn sharply to flow along the impaction surface 130. This promotes deposition of aerosol components onto the impaction surface 130 in use. Larger or heavier aerosol components may not be able to change direction quickly enough and will be deposited onto the impaction surface 130 by impaction. It will be understood that the tightness of the turn required and the flow velocity of the aerosol sample will determine the size and/or mass above which aerosol components will be deposited by impaction on the impaction surface 130. For example, where the impaction surface 130 is located further from the flow constrictions 126, the flow speed will have reduced, and aerosol components will need to be bigger and/or heavier in order to be deposited out of the aerosol sample by impaction. Similarly, where the flow constrictions 126 are narrower, the flow speed will be increased and aerosol components having smaller sizes and/or masses will be deposited out of the aerosol sample by impaction onto the impaction surface 130.

In this example, a cross-sectional area of the aerosol inlet 110 is substantially the same as the total cross-sectional area of the combination of the flow constrictions 126 through the single impactor component 128. It will be understood that any reduction in the cross-sectional area of either the aerosol inlet 110 or the total cross-sectional area of the combination of the flow constrictions 126 may increase a resistance to breathing when the impactor apparatus 100 is used for collecting components of exhaled breath.

In this example, the impactor component 128 is in the form of a container, for example a shallow container, and the impaction surface 130 is provided by a base of the container. Thus, the impaction surface 130 is an impaction plate in this example. In this example, the impaction surface 130 is a flat surface. In other examples, it will be understood that the impaction surface 130 may be a patterned surface whereby to increase a surface area of the impaction surface 130, or to modify a flow characteristic of the aerosol sample following the aerosol flow path 124 onto the impaction surface 130. For this purpose, in example, the impaction surface 130 may have defined therein invaginations, flanges, scalloping, or any other defined or chaotic surface features.

In order to prevent contamination or escape of the aerosol components collected by impaction on the impaction surface 130, the impactor apparatus 100 also comprises a sealing component (not shown in FIG. 2) for sealing around the impaction surface 130 of the impactor component 128. The sealing component is changeable from a sample collection configuration in which the impaction surface 130 is exposed for aerosol component collection to a sample containment configuration in which the impaction surface 130 is isolated form the external environment. It will be understood that FIG. 2 shown the sealing component in a sample collection configuration with the impaction surface 130 exposed for aerosol component collection.

It will be understood that the size of the flow constrictions 126 can vary as required to cause deposition of aerosol components onto the impaction surface 130. In this example, the flow constrictions each has a diameter of 2 millimetres.

Figure 3:
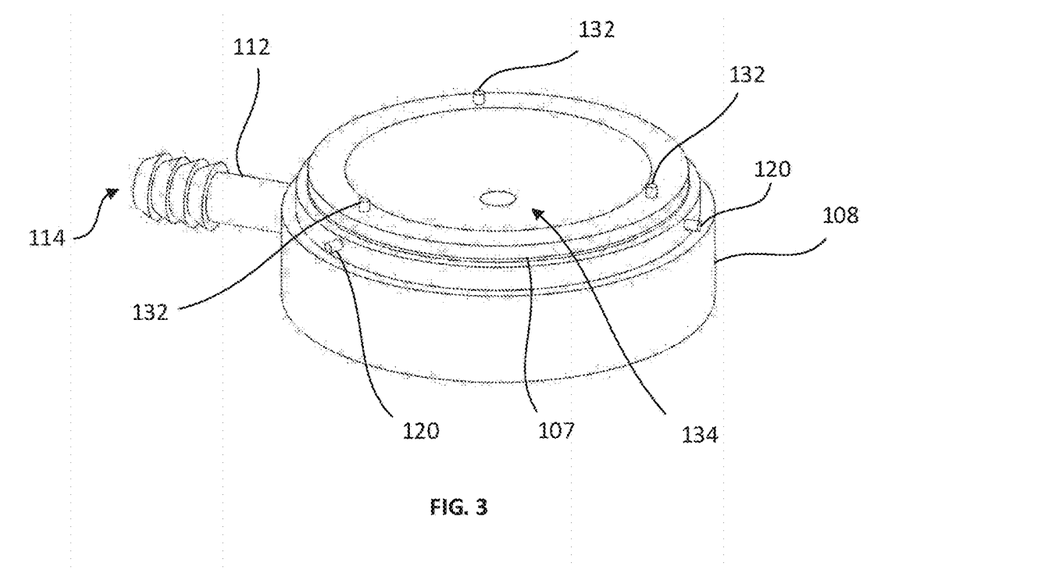
FIGS. 3 to 8 illustrate an assembly of the impactor apparatus shown in FIGS. 1 and 2.

The assembly and operation of an example impactor apparatus 100 will now be described with reference to FIGS. 3 to 8. FIG. 3 shows the outlet housing portion 108. To assemble the impactor apparatus 100, the outlet housing portion 108 is first located on a working surface. If required, the outlet pipe 112 can be connected to any further devices for further fluid communication with the aerosol outlet 114. The aerosol outlet 114 is in fluid communication with an outlet housing portion inlet 134. As described previously, the outlet housing portion 108 comprises three outlet housing protrusions 120 circumferentially spaced around the side wall of the outlet housing portion 108. The outlet housing portion 108 further comprises a spacing portion in the form of three spacing members 132 to space the impactor component 128 (not shown in FIG. 3) away from an upper surface of the outlet housing portion 108 by approximately 3 millimetres in the present example, whereby to allow aerosol flow around an outside of the impactor component 128 and into the outlet housing portion inlet 134. In this example, the three spacing members 132 are arranged to at least partially engage with a plurality of indentations (not shown) defined in the outer surface of a base portion of the impactor component 128. In this way, the impactor component 128 can be biased into a preferred orientation relative to the housing assembly 102, in particular, relative to the outlet housing portion 108 and the impactor housing portion 106. In some examples, the spacing members 132 are adjustable in height, whereby to alter a spacing of the impactor component 128 from the outlet housing portion 108.

Figure 4:
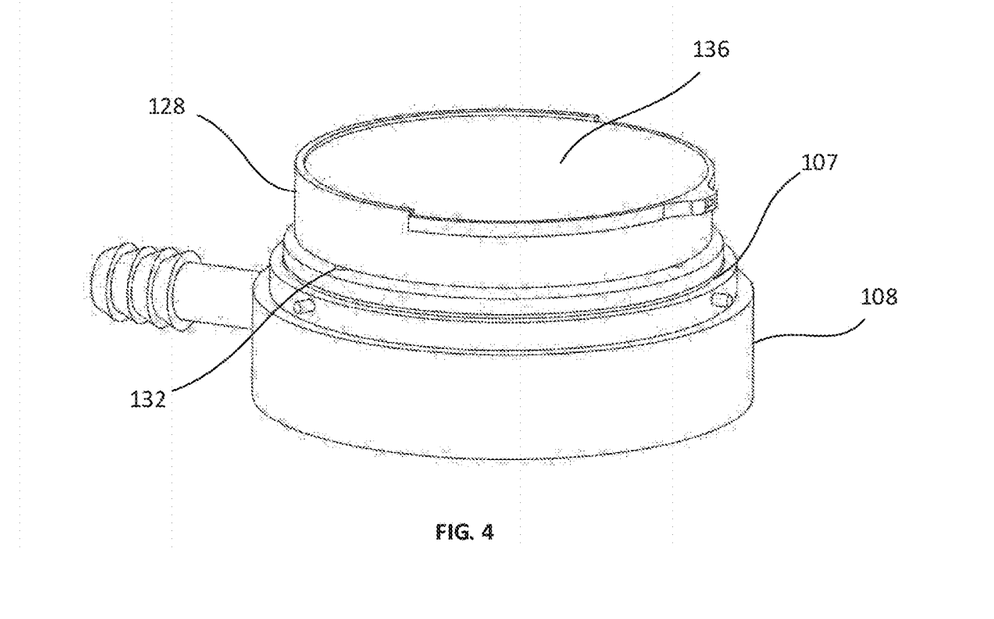

FIG. 4 shows the outlet housing portion 108 as shown in FIG. 3, with the addition of the impactor component 128 provided on the spacing members 132 of the outlet housing portion 108. The impactor component 128 is provided in combination with a sealing component in the form of a cover member such as a lid 136 to isolate an impaction surface (not shown in FIG. 4) of the impactor component 128 from the external environment. Thus, the impactor component 128 can be provided initially in a sealed configuration whereby to substantially prevent any external contamination of the impactor components 128.

In some examples, the lid 136 may be have a penetrable section (sometimes referred to as a septum) provided therein to allow sampling of any aerosol components collected on the impaction surface without unsealing the impaction surface of the impactor component 128.

Figure 5:
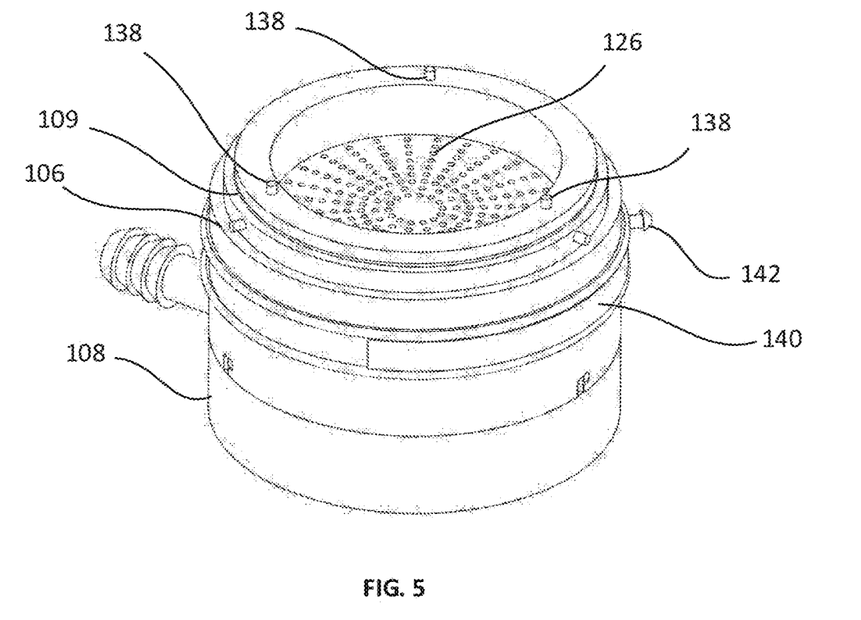

As shown in FIG. 5, the impactor housing portion 106 is next assembled onto the outlet housing portion 108 to substantially enclose the impactor component 128. Thus, the aerosol outlet 114 is in fluid communication with the flow constrictions 126 of the impactor housing portion 106 through the impactor apparatus 100. The impactor housing portion 106 has defined in a side wall thereof a lid removal opening for removal of the lid 136 of the impactor component 128 when the impactor apparatus 100 is assembled. In the present example, the lid removal opening is covered by an opening cover 140 which is slidably mounted to the side wall of the impactor housing portion 106 and is provided with a handle 142 which can be used to slide the opening cover 140 to expose the lid removal opening (see FIG. 6). As with the outlet housing portion 108, the impactor housing portion 106 further comprises a spacing portion in the form of three spacing members 138 to space any further impactor components (see FIG. 10) away from the impactor housing portion 106 whereby to allow airflow around an outer edge of the impactor component through the impactor apparatus 100.

In this example, the inlet housing portion 104 is next assembled onto the impactor housing portion 106 to provide a complete impactor apparatus 100, having a single impaction stage, as shown in FIG. 1. Thus, the impactor apparatus 100 can be fully assembled while maintaining the impactor component 128 in a sealed configuration.

Figure 6:
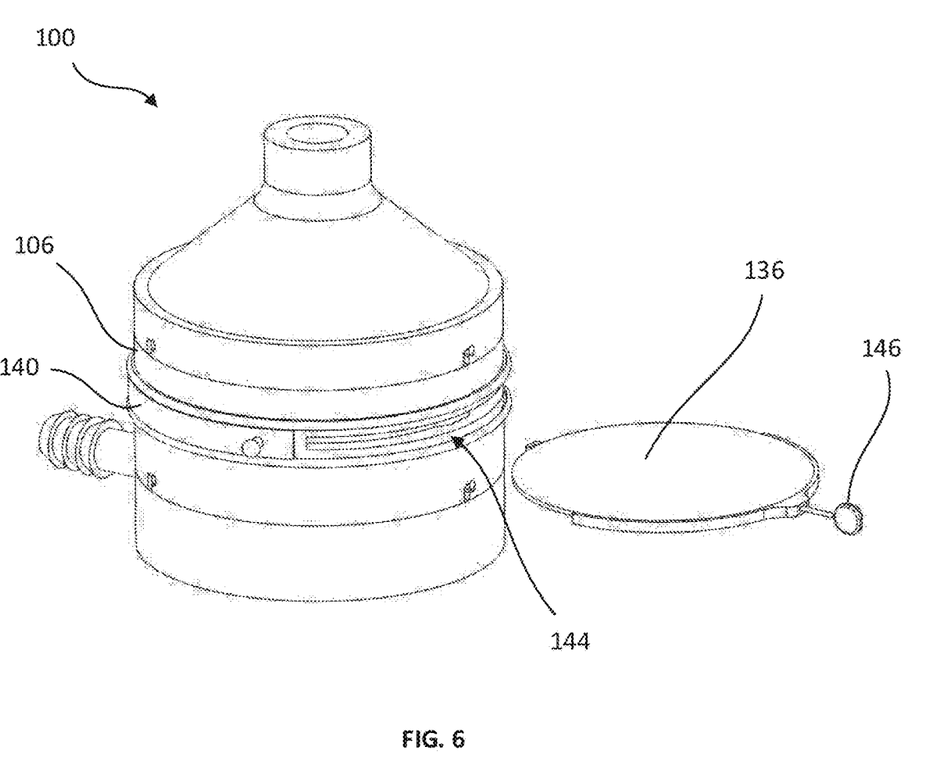
Figure 7:
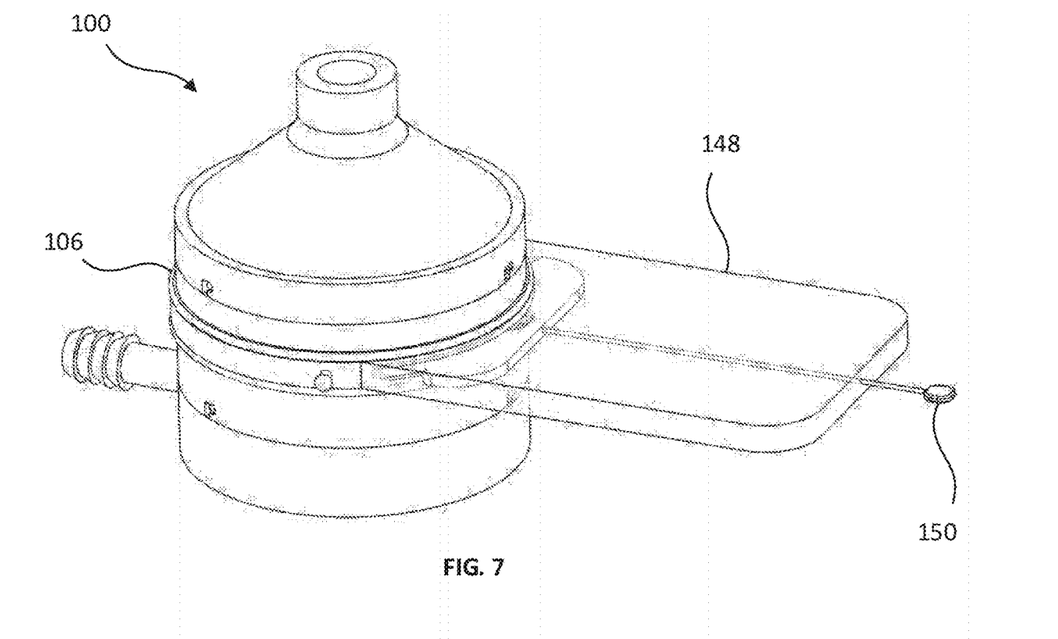

To provide the impactor apparatus 100 in a sample collection configuration, the opening cover 140, if present, must first be moved to expose a lid removal opening 144 in the impactor housing portion 106 as shown in FIG. 6. Next, the sealing component, in the form of the lid 136, must be removed from the impactor component 128 in order to expose the impaction surface 130 for aerosol component collection. It will be understood from FIGS. 4 and 6 that the indentations in the outer surface of the base portion of the impactor component 128 ensure that an orientation of the impactor component 128 on the spacing members 132 is such that the lid 136 can be removed through the lid removal opening 144. The engagement of the spacing member 132 within the indentations on the outer surface of the impactor component 128 further ensure that the impactor component 128 does not slide towards an internal surface of the impactor housing portion 106 during removal of the lid 136 from the impactor component 128. In the present example, the lid 136 can be easily slid off the impactor component 128 using a lid removal tool 146 which is removably attachable to the lid 136 for easily moving the lid 136, even when the impactor component 128 is contained within the impactor housing portion 106. In some examples, the lid 136 is completely removed from the impactor apparatus 100 and stored elsewhere during aerosol component collection. Alternatively, as shown in FIG. 7, the lid 136 can be removed into a lid extraction component 148 (show as transparent in FIG. 7) which can store the lid 136 in a substantially sterile and/or sealed environment during sample collection to substantially prevent contamination of the aerosol component sample after sample collection. The lid extraction component 148 attached to the impactor housing portion 106 around the lid removal opening 144. An extraction component lid removal tool 150 is provided and is similar to the lid removal tool 146 shown in FIG. 6. In particular, the extraction component lid removal tool 150 is attachable to an edge of the lid 136, whereby to slide the lid 136 off the impactor component 128 contained within the impactor housing portion 106. As will be understood, the extraction component lid removal tool 150 can also be used for moving the lid 136 onto the impactor component 128 to provide the sealing component in the sample containment configuration.

Figure 8:
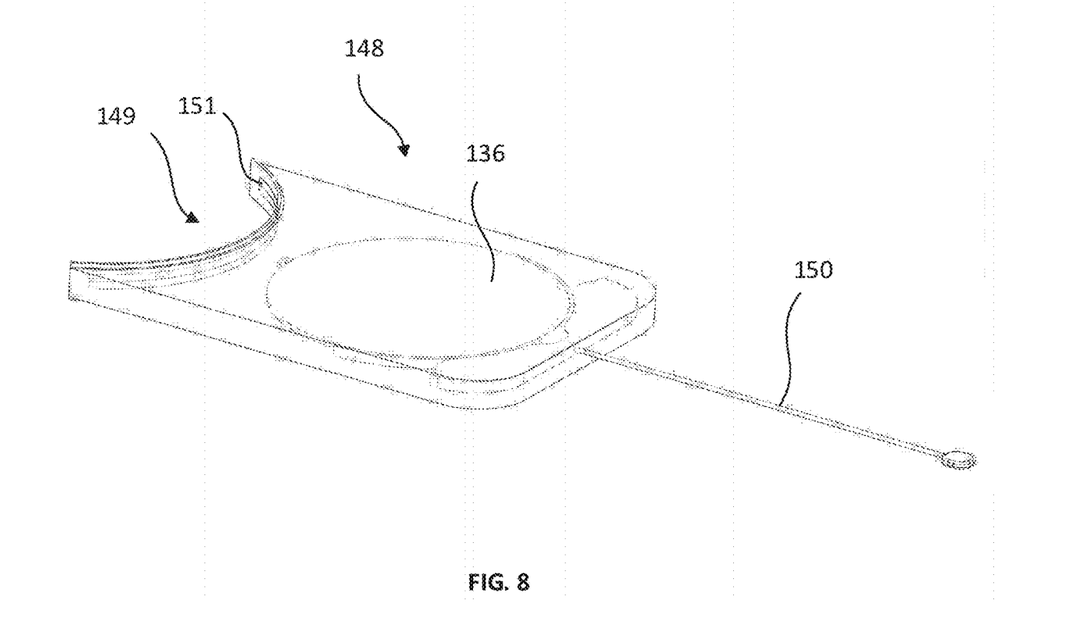

FIG. 8 shows the lid extraction component 148 shown in FIG. 7, with the lid 136 stored therein. As in FIG. 7, the lid extraction component 148 is shown in transparent to facilitate visibility of the lid 136 through the lid extraction component 148. The lid extraction component 148 is configured to attach to the impactor housing portion 106 around the lid removal opening 144. An entrance portion 149 of the lid extraction component 148 is covered by a seal member 151. Thus, when the lid 136 is stored within the lid extraction component 148, the lid 136 can be sealed from the external environment which substantially prevents contamination of any deposits on the impaction surface 130 when the lid 136 is replaced onto the impactor component 128 for removal of the sample from the impactor apparatus 100. As explained in relation to FIG. 7 above, the extraction component lid removal tool 150 is attached to the edge of the lid 136 for removal and replacement of the lid 136 on the impactor component 128.

Figure 9:
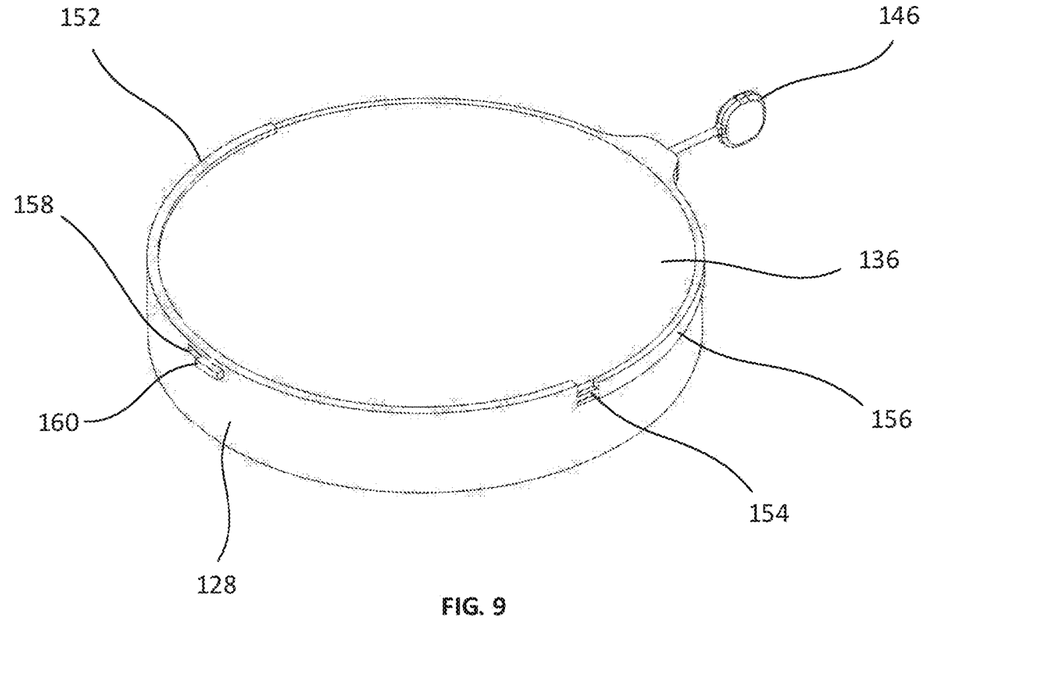
FIG. 9 shows the lid extraction component shown in FIG. 8, having the lid stored therein.

FIG. 9 shows the impactor component 128 with the lid 136 provided in a locked configuration. In this example, the lid 136 is sealed around an impaction surface of the impactor component 128. In particular, a distal end of the lid 136 is engaged within a groove defined by a lip 152 extending radially inwardly from a portion of a top of a side wall of the impactor component 128. Further, the lid 136 also comprises a lip portion 156 at a proximal end of the lid 136 and defining a groove to receive an impactor component protrusion 154 therein. When the lid 136 is fully engaged on the impactor component 128, a locking tab 160, extending from the distal end of the lid 136, is inserted in a locking opening 158 defined in the side wall of the impactor component 128. Further, the locking tab 160 has a substantially dog-leg shape, whereby a sliding movement of the lid 136 in a counter-clockwise direction (in the present example), engages the locking tab 160 with an edge of the locking opening 158, whereby to secure the lid 136 in place on the impactor component 128 to seal around the impaction surface 130. In the present example shown in FIG. 9, it will be understood that pushing the lid removal tool 146 left will unlock the locking tab 160 from the locking opening 158 and allow the lid 136 to be slid off and away from the impactor component 128. Similarly, when unlocked, pushing the lid removal tool 146 in a rightwards direction when the lid 136 is fully slid onto the impactor component 128 will lock the lid 136 in place on the impactor component 128 and substantially prevent accidental removal of the lid 136, thereby ensuring no contamination of the impactor surface 130 during transport or storage of the impactor component 128 outside the impactor apparatus 100.

Once sample collection is complete, the impactor component 128 needs to be locked into a sample containment configuration to retain any aerosol components deposited on the impaction surface 130. This can be done using the sealing mechanism in the form of the lid 136 and sealing the lid 136 onto the impactor component 128. It will be understood that this is substantially in reverse to removal of the lid 136, as described previously. For subsequent analysis of any aerosol components deposited on the impaction surface 130, the sealed impactor component 128 first needs to be removed from the impactor apparatus 100. The sealed impactor component 128 is removed from the impactor apparatus 100 by disassembly of the impactor apparatus 100, substantially by reversing the process described previously. Thus, the inlet housing portion 104 and the impactor housing portion 106 are removed (either together or sequentially) from the housing portion acting as a base support for the impactor component 128. In this example, the impactor housing portion 106 is removed from the outlet housing portion 108, whereby to allow removal of the sealed impactor component 128 from the impactor apparatus 100.

Figure 10:
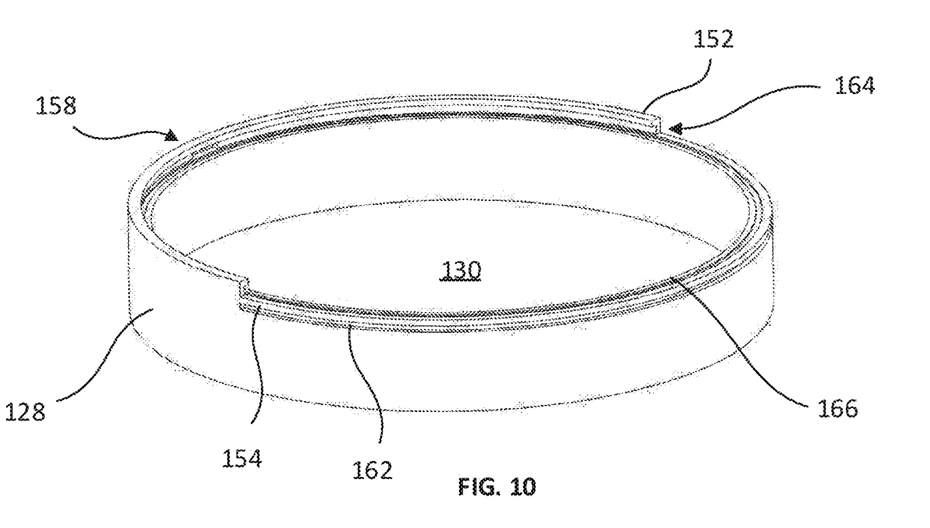
FIG. 10 shows the impactor component without the lid shown in FIG. 9.

FIG. 10 shows the impactor component 128 without the lid 136 shown in FIG. 9. As shown in FIG. 9, a distal end, in this example, substantially half, of the side wall of the impactor component 128 is capped by the lip 152 extending radially inwardly. The lip 152 defines an upper groove 164 for receiving a distal end of the lid 136, as shown in FIG. 9, such that the locking tab 160 of the lid 136 can be received in the locking opening 158 of the impactor component 128. The impactor component protrusion 154 extends radially outward from the impactor component 128 over a proximal end, in this example, substantially half, of the side wall of the impactor component 128. The impactor component protrusion 154 and a lower portion of the side wall together define a proximal groove 162 in the proximal end of the side wall of the impactor component 128 to receive the lip portion 156 of the lid 136. Thus, the lid 136 provides a sealing mechanism to engage over the impaction surface 130 of the impactor component 128 to isolate the impaction surface 130 from the external environment and ensure any aerosol components deposited on the impaction surface are retained thereon. In this example, a sealing member 166 is provided between the lid 136 and the impactor component 128 to ensure an airtight seal of the impaction surface 130 from the external environment. In particular, the sealing member 166 in this example is a neoprene seal ring, provided around the side wall of the impactor component to be in contact with an underside of the lid 136.

Figure 11:
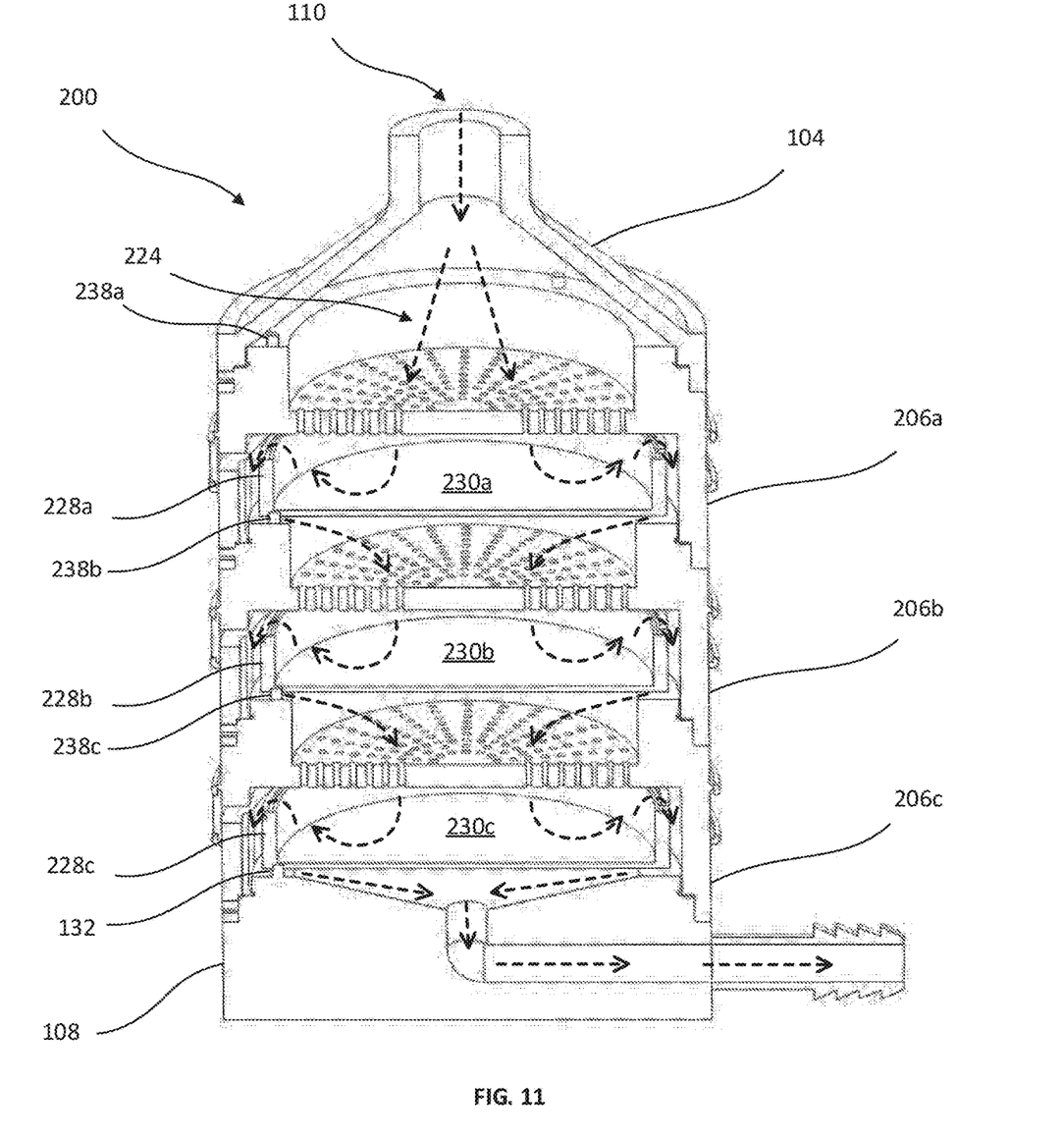
FIG. 11 shows a cross-section through a further example of an impactor apparatus.

FIG. 11 shows a cross-section through a further example of an impactor apparatus 200, similar to that shown in FIGS. 1 to 9, but having three impactor components 228a, 228b, 228c each within a respective impactor housing portion 206a, 206b, 206c instead of the single impactor component 128 within the single impactor housing portion 106 shown in the example of FIGS. 1 to 9. In particular, FIG. 11 shows an aerosol flow path 224 through the impactor apparatus 200 when a sealing component of the impactor apparatus 200 is in a sample collection configuration to expose impaction surfaces 230a, 230b, 230c of each of the impactor components 228a, 228b, 228c to the aerosol sample. The lowermost impactor component 228c is spaced from the outlet housing portion 108 on the spacing members 132, substantially as described with reference to FIGS. 3 and 4 hereinbefore. The remaining impactor components 228a, 228b are spaced from the respective upper surface of the impactor housing portions 206c, 206b by the spacing members 238c, 238b, provided to extend substantially upwards from the upper surface of the impactor housing portions 206c, 206b. It will be understood that the assembly and operation of the impactor apparatus 200 is substantially similar to that described with reference to FIGS. 1 to 9 above, apart from the hereinbefore noted differences.

In summary, there is provided a kit of parts for assembly into an impactor (100) for aerosol component collection, such as for exhaled breath. The kit comprises a housing (104, 106, 108) configured to define an aerosol inlet (110) for receiving an aerosol sample in use and, when the kit of parts is assembled into the impactor (100), to define at least in part an aerosol flow path (124) from the aerosol inlet (110) through the impactor apparatus (100). The kit further comprises an impactor component (128) receivable into an assembly providing the impactor apparatus (100). The assembly comprises at least the housing (104, 106, 108). The impactor component (128) has an impaction surface (130) onto which one or more aerosol components from the aerosol sample are to be deposited in use. The kit further comprises a sealing component (136) for sealing around the impaction surface (130) of the impactor component (128). The sealing component (136) is changeable from a sample collection configuration in which the impaction surface (130) is exposed for aerosol component collection to a sample containment configuration in which the impaction surface (130) is isolated from the external environment. The kit of parts is configured such that the impactor component (128) is receivable into the assembly such that, when the sealing mechanism (136) is in the sample collection configuration and an aerosol sample is being received at the aerosol inlet (110) in use, the aerosol flow path (124) of the aerosol sample is directed onto the impaction surface (130) to promote aerosol deposition thereon. The kit of parts is further configured such that the sealing component (136) is changeable in the assembly into the sample containment configuration before removal of the impactor component (128) from the assembly, so as to retain any aerosol components deposited on the impaction surface (130).

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The invention claimed is:

1. A kit of parts for assembly into an impactor for aerosol component collection, such as for exhaled breath, the kit comprising:
   a housing configured to define an aerosol inlet for receiving an aerosol sample in use and, when the kit of parts is assembled into the impactor, to define at least in part an aerosol flow path from the aerosol inlet through the impactor apparatus;
   an impactor component receivable into an assembly providing the impactor apparatus, the assembly comprising at least the housing, and the impactor component having an impaction surface onto which one or more aerosol components from the aerosol sample are to be deposited in use; and
   a sealing component for sealing around the impaction surface of the impactor component, the sealing component being changeable from a sample collection configuration in which the impaction surface is exposed for aerosol component collection to a sample containment configuration in which the impaction surface is isolated from the external environment;
   the kit of parts being configured such that:
      the impactor component is receivable into the assembly such that, when the sealing mechanism is in the sample collection configuration and an aerosol sample is being received at the aerosol inlet in use, the aerosol flow path of the aerosol sample is directed onto the impaction surface to promote aerosol deposition thereon; and
      such that the sealing component is changeable in the assembly into the sample containment configuration before removal of the impactor component from the assembly, so as to retain any aerosol components deposited on the impaction surface.

2. A kit of parts as claimed in claim 1, wherein one or more parts of the kit of parts separately or together provides a sealing mechanism which is configured and/or operable such that the sealing component is moved or caused to be moved into the sample containment configuration after sample collection before the impactor component is fully removed from the assembly.

3. A kit of parts as claimed in claim 1, wherein the housing comprises an inlet housing portion, defining the aerosol inlet therein.

4. A kit of parts as claimed in claim 1, wherein the housing comprises an outlet housing portion, defining an aerosol outlet therein, and wherein the aerosol outlet is in fluid communication with the aerosol inlet through the impactor apparatus when the kit of parts is assembled.

5. A kit of parts as claimed in claim 1, wherein the housing comprises at least one impactor housing portion to receive the impactor component therein during assembly of the kit of parts.

6. A kit of parts as claimed in claim 1, wherein the impactor component is a shallow dish.

7. A kit of parts as claimed in claim 6, wherein the impaction surface is provided by a base surface of the dish.

8. A kit of parts as claimed in claim 1, wherein the assembly providing the impactor apparatus has defined therein a plurality of flow constrictions to generate a high-velocity aerosol flow onto the impaction surface in the aerosol flow path.

9. A kit of parts as claimed in claim 8, wherein the plurality of flow constrictions is at least ten flow constrictions.

10. A kit of parts as claimed in claim 8, wherein the plurality of flow constrictions are defined in the housing.

11. A kit of parts as claimed in claim 1, wherein the kit of parts comprises a plurality of the impactor components each receivable into the assembly to be arranged in the assembly together successively in the flow path.

12. A kit of parts as claimed in claim 1, wherein the assembly is configured such that, in the sample collection configuration, the aerosol flow path directed onto the impaction surface of the impactor component is directed, downstream, around an outer edge of the impactor component through the impactor apparatus.

13. A kit of parts as claimed in claim 1, wherein the sealing component is a cover member to cover the impaction surface when the sealing component is in the sample containment configuration and wherein the sealing component is movable from the sample collection configuration to the sample containment configuration.

14. A kit of parts as claimed in claim 13, wherein the cover member is slidable to move from an uncovered position allowing the aerosol flow path to be directed onto the impaction surface in the sample collection configuration to a covered position in which the cover member covers the impaction surface in the sample containment configuration to retain any aerosol components deposited on the impaction surface.

15. A kit of parts as claimed in claim 14, wherein the housing has defined therein an opening for passage therethrough of the cover member onto the impactor component during movement from the sample collection configuration to the sample containment configuration.

16. A kit of parts as claimed in claim 1, wherein the or a further sealing component of the kit of parts is for sealing around the impaction surface of the impactor component and the kit of parts is configured such that the or the further sealing component is changeable from a sealed configuration in which the impaction surface is isolated from the external environment to the sample collection configuration in which the impaction surface is exposed for aerosol collection.

17. A kit of parts as claimed in claim 16, wherein the or the further sealing component is a cover member to cover the impaction surface when the sealing component is in the sealed configuration and wherein the sealing component is movable from the sealed configuration to the sample collection configuration.

18. An impactor apparatus for aerosol component collection and formed from the kit of parts as claimed in claim 1.

19. A method of collecting aerosol components from an aerosol sample in an impactor apparatus, the method comprising:
assembling the impactor apparatus from at least a housing to receive an impactor component within the impactor apparatus, the housing defining, at least in part, an aerosol flow path from the aerosol inlet through the impactor apparatus, the impactor component having an impaction surface onto which one or more aerosol components from the aerosol sample are to be deposited in use, and being provided with a sealing component for sealing around the impaction surface of the impactor component, the sealing component in a sample collection configuration in which the impaction surface is exposed for aerosol component collection, wherein the aerosol flow path of the aerosol sample is directed onto the impaction surface to promote aerosol deposition thereon;
supplying an aerosol sample to an aerosol inlet of a housing of the impactor apparatus to deposit one or more aerosol components of the aerosol sample onto the impaction surface; and
changing the sealing component from the sample collection configuration to a sample containment configuration in which the impaction surface is isolated from the external environment,
wherein the sealing component is changed from the sample collection configuration into the sample containment configuration before removal of the impactor component from the assembly, so as to retain any aerosol components deposited on the impaction surface.

* * * * *